United States Patent
Heismann et al.

(10) Patent No.: US 8,005,183 B2
(45) Date of Patent: Aug. 23, 2011

(54) COMPUTED TOMOGRAPHY DEVICE WITH ACTIVE ADAPTATION OF THE MEASURING ELECTRONICS

(75) Inventors: Bjoern Heismann, Erlangen (DE); Erhard Schlund, Effeltrich (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 2717 days.

(21) Appl. No.: 10/342,250

(22) Filed: Jan. 15, 2003

(65) Prior Publication Data

US 2010/0111247 A1 May 6, 2010

(30) Foreign Application Priority Data

Jan. 15, 2002 (DE) .................................. 102 01 321

(51) Int. Cl.
*A61B 6/00* (2006.01)
(52) U.S. Cl. ............................................................ 378/4
(58) Field of Classification Search ................ 378/4, 156
See application file for complete search history.

(56) References Cited

U.S. PATENT DOCUMENTS

| | | | | |
|---|---|---|---|---|
| 4,066,902 A | * | 1/1978 | LeMay | 378/12 |
| 4,091,289 A | * | 5/1978 | LeMay | 378/7 |
| 4,333,145 A | * | 6/1982 | Heuscher et al. | 600/425 |
| 4,380,817 A | * | 4/1983 | Harding et al. | 378/87 |
| 4,637,040 A | * | 1/1987 | Sohval et al. | 378/9 |
| 4,707,786 A | * | 11/1987 | Dehner | 378/14 |
| 4,729,100 A | * | 3/1988 | Tsujii | 378/4 |
| 4,773,086 A | | 9/1988 | Fujita et al. | |
| 5,012,498 A | | 4/1991 | Cuzin et al. | |
| 5,359,638 A | * | 10/1994 | Hsieh et al. | 378/4 |
| 5,361,291 A | * | 11/1994 | Toth et al. | 378/12 |
| 5,416,815 A | * | 5/1995 | Hsieh | 378/4 |
| 5,416,817 A | * | 5/1995 | Ruehrnschopf | 378/19 |
| 5,818,896 A | * | 10/1998 | Hsieh | 378/15 |
| 5,841,829 A | * | 11/1998 | Dolazza et al. | 378/4 |
| 5,963,614 A | | 10/1999 | Hu et al. | |
| 6,173,039 B1 | * | 1/2001 | Hampel et al. | 378/150 |
| 6,175,609 B1 | * | 1/2001 | Edic et al. | 378/7 |
| 6,304,625 B1 | * | 10/2001 | Senzig | 378/4 |
| 6,415,012 B1 | * | 7/2002 | Taguchi et al. | 378/15 |
| 6,470,067 B1 | * | 10/2002 | Harding | 378/19 |
| 6,990,171 B2 | * | 1/2006 | Toth et al. | 378/16 |
| 7,376,255 B2 | * | 5/2008 | De Man et al. | 382/131 |
| 7,440,598 B2 | * | 10/2008 | Bruder et al. | 382/128 |
| 7,515,689 B2 | * | 4/2009 | Baba et al. | 378/156 |
| 2001/0004393 A1 | * | 6/2001 | Klingenbeck-Regn | 378/19 |
| 2002/0018540 A1 | * | 2/2002 | Stierstorfer | 378/16 |
| 2002/0037067 A1 | * | 3/2002 | Horiuchi | 378/4 |
| 2002/0131549 A1 | * | 9/2002 | Oikawa | 378/19 |
| 2002/0150200 A1 | * | 10/2002 | Zonneveld | 378/4 |
| 2003/0053597 A1 | * | 3/2003 | Flohr et al. | 378/156 |

FOREIGN PATENT DOCUMENTS

DE 19854471 5/1999

\* cited by examiner

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

A computed tomography device (CT device) includes a user interface, via which the standard settings characterizing the CT measurement can be performed. At the same time, in a method and a computed tomography device for carrying out this method, filtering behavior of the filter electronics is adapted to the configuration of the standard settings by the system computer.

31 Claims, 3 Drawing Sheets

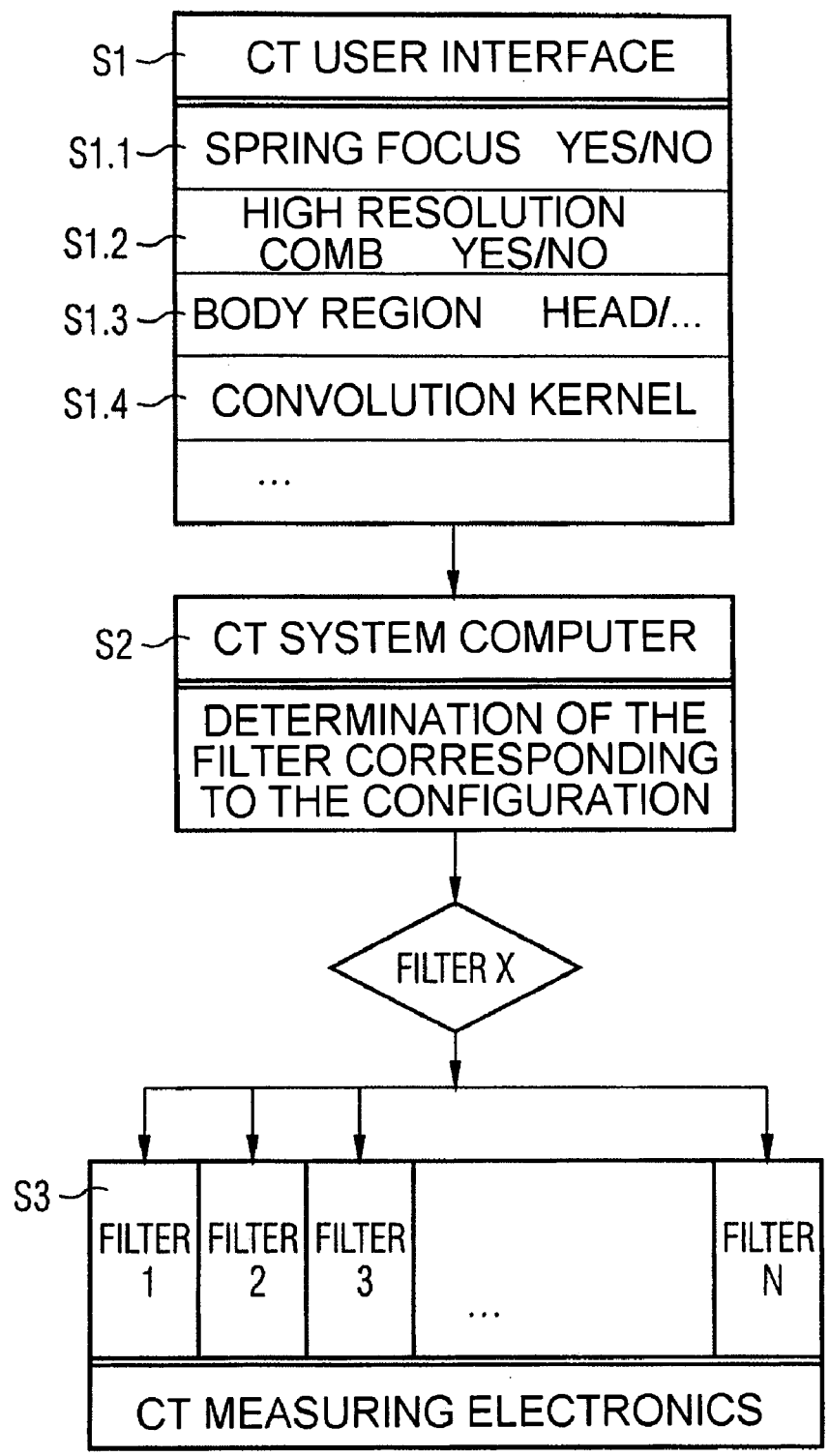

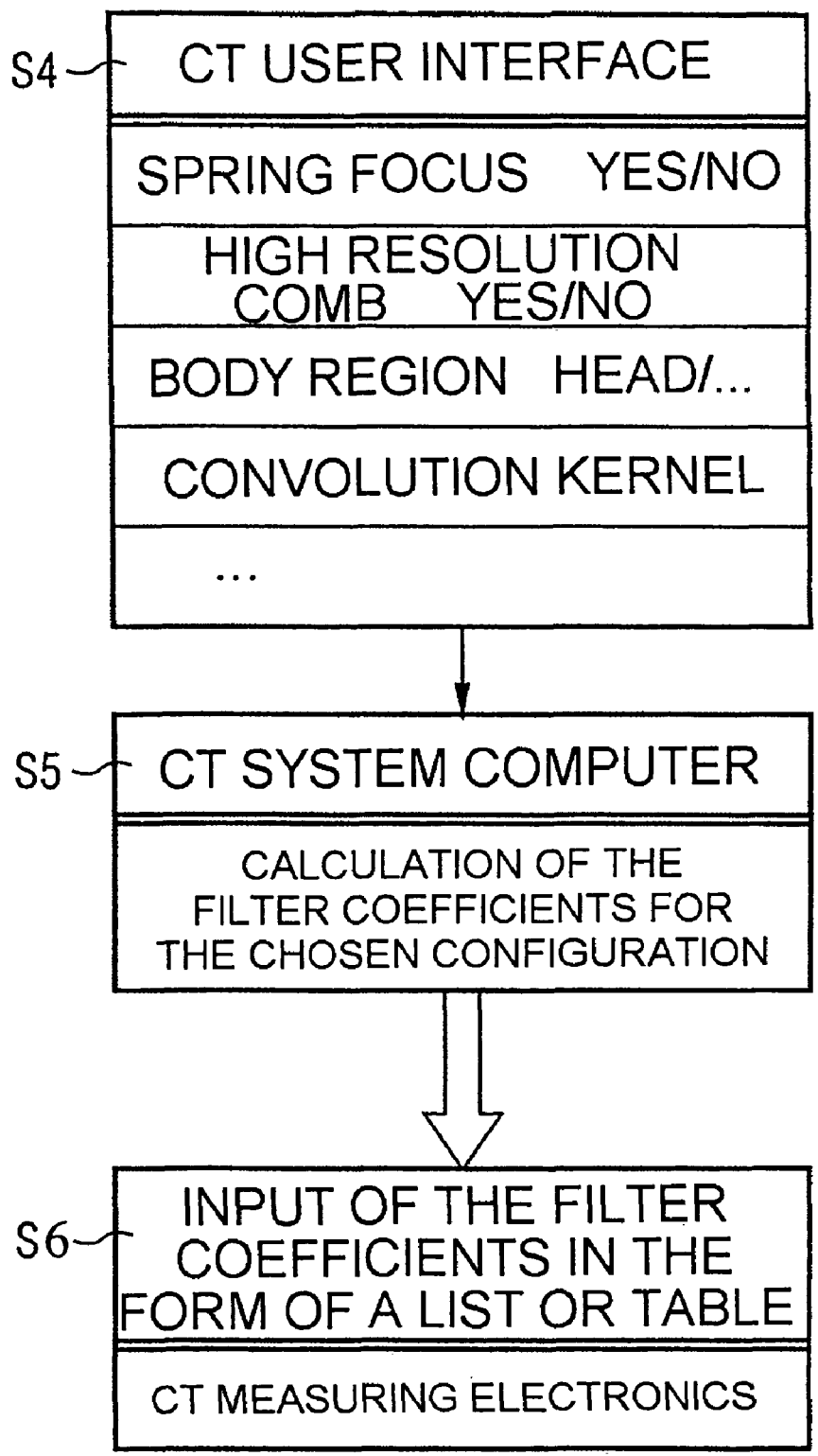

COMPUTED TOMOGRAPHY DEVICE WITH ACTIVE ADAPTATION OF THE MEASURING ELECTRONICS

The present application hereby claims priority under 35 U.S.C. §119 on German patent application number 10201321.7 filed Jan. 15, 2002, the entire contents of which are hereby incorporated herein by reference.

FIELD OF THE INVENTION

The present invention generally relates to a computed tomography device (CT device) which has a user interface, via which the standard settings characterizing the CT measurement can be performed. At the same time, the present invention generally relates in particular to a method and a computed tomography device for carrying out this method, in which the filtering behavior of the filter electronics is adapted to the configuration of the standard settings by the system computer.

BACKGROUND OF THE INVENTION

With modern methods of medical diagnosis, such as for example X-ray computed tomography (CT), image data of an examined object of measurement can be obtained. The examined object of measurement is generally a patient.

X-ray computed tomography—referred to hereafter as CT for short—is a special method of radiography which differs in principle from the classic method of tomography in the construction of the image. In the case of CT scans, transversal sectional images are obtained, that is to say images of sections of a body, which are oriented substantially perpendicular to the axis of the body. The tissue-specific physical variable represented in the image is the distribution of the attenuation of X-radiation $\mu(x,y)$ in the sectional plane. The CT image is obtained by a reconstruction of the one-dimensional projections, supplied by the measuring system used, of the two-dimensional distribution of $\mu(x,y)$ from numerous different viewing angles.

The projection data are determined from the intensity I of an X-ray beam after it has passed through the layer of which an image is to be formed and its original intensity $I_0$ at the X-ray source according to the law of absorption $$\ln\frac{I}{I_0} = -\int_L \mu(x,y)dl \quad (1)$$

The path of integration L represents the path of the X-ray beam under consideration through the two-dimensional attenuation distribution $\mu(x,y)$. An image projection is then made up from the measured values of the line integrals through the object layer, obtained with the X-rays of a viewing direction.

The projections—characterized by the projection angle $\alpha$—originating from many different directions are obtained by a combined X-ray tube detector system, which rotates around the object in the plane of the layers. The devices which are most commonly used at present are known as "fan beam devices", in which a tube and an array of detectors (a linear or part-circular arrangement of detectors) rotate together in the plane of the layers about a center of rotation, which is also the center of the circular measurement field. The "parallel beam devices", which have very long measuring times, are not explained here. However, it should be pointed out that a transformation from fan projections to parallel projections and vice versa is possible, so that the present invention, which is to be explained on the basis of a fan beam device, can also be used for parallel beam devices without any restriction.

In FIG. 1, a computed tomography device for a fan beam method is schematically represented. In the case of this device, X-ray tubes 1 and beam receivers 2 (detectors) rotate together about a center of rotation, which is also the center of the circular measurement field 5, and in which the patient 3 to be examined is lying on a patient bench 4. To allow different parallel planes of the patient 3 to be examined, the patient bench can be displaced along the longitudinal axis of the body. The advancement of the patient bench is generally referred to as "pitch".

As can be seen from the drawing, CT scans produce transversal sectional images, that is images of layers of the body which are oriented substantially perpendicular to the axis of the body. This method of layered representation presents the distribution of the attenuation value $\mu_z(x,y)$ itself (z is the position on the longitudinal axis of the body).

Computed tomography (referred to hereafter as CT) requires projections from very many angles $\alpha$. To generate a tomogram, the cone of rays emitted by the X-ray tube 1 is masked in such a way as to produce a planar fan of rays, which casts one-dimensional central projections of the radiographed layer. For the exact reconstruction of the distribution of the attenuation values $\mu_z(x,y)$, this fan of rays must be perpendicular to the axis of rotation and also spread so wide that it completely covers the layer aimed at of the object of measurement from every direction of projection $\alpha$. This fan of rays passing through the object is picked up by detectors, which are arranged linearly on a segment of a circle. In the case of commercially available devices, there are up to 1000 detectors. The individual detector reacts to the incident rays with electrical signals, the amplitude of which is proportional to the intensity of these rays.

Each individual detector signal belonging to a projection $\alpha$ is in each case picked up by measuring electronics 7 and passed on to a computer (system computer) 8. With the computer 8, the measured data can then be processed in a suitable way and visually displayed on a monitor 6, initially in the form of a sinogram (in which the projection $\alpha$ is plotted as a function of the measured values of the corresponding channel $\beta$) in what are known as Gordon units, but finally in the form of a natural X-ray image in Hounsfield units.

According to the prior art, the person operating the CT device (generally the doctor) must perform settings on the CT device in order to achieve the desired image quality, which, inter alia, is also characterized by the contrast or the signal-to-noise ratio.

At the present point in time, these setting possibilities are very elementary. Current intensity, voltage, region of the patient to be recorded, layer thickness, pitch, etc., can be set. It is also possible to set whether the CT device is operated in spring focus or with a high-resolution comb. Both operating modes are explained in more detail later.

The disadvantage here is that the frequency response of the measuring electronics cannot be adapted to the chosen settings, as a result of which the entire informational content of the CT signal cannot be interpreted. In order nevertheless to obtain approximately the desired image quality, the signals obtained are processed after measurement by additional low-pass or high-pass filters. As stated, this is only possible in an approximate manner, since the electronics available for subsequent processing are predetermined by hardware and do not allow any latitude.

SUMMARY OF THE INVENTION

An object of an embodiment of the present invention is therefore to provide a computed tomography device in which the informational content of the CT measurement signal is better utilized.

It is possible, in particular in one embodiment of the invention, for the dose of the X-radiation to be reduced while retaining the same image quality, by adapting the measuring electronics to the configuration of the CT device.

Consequently, an embodiment of the invention proposes a computed tomography device (CT device), having an X-ray tube for radiographing an object to be examined with X-radiation and a beam receiver for measuring the X-radiation transmitted through the object and for outputting measurement signals. Furthermore, the CT device has a user interface, via which a number of standard settings of the device characterizing the measurement can be set in the form of different evaluation and scanning parameters. In addition, the CT device according to an embodiment of the invention includes measuring electronics, which include configurable filter electronics for filtering and preparing the measurement signals. It also includes a system computer for configuring the filter electronics on the basis of the standard settings set before the measurement via the user interface and for evaluating the measurement results.

In a first embodiment of the invention, the configuration of the filter electronics takes place by selection of a filter from a number of filters present in the filter electronics.

In a second embodiment of the invention, the configuration of the filter electronics takes place by the calculation of filter coefficients, the filtering behavior of the filter electronics being determined by these filter coefficients.

Of the standard settings already mentioned above, according to an embodiment of the invention one or more of the following settings can be performed:

measurement takes place in spring focus mode or not,
measurement takes place in a high-resolution comb or not,
designation of the body region to be measured,
setting of the convolution kernel.

Furthermore, an embodiment of the invention proposes a method of computed tomography imaging which has the following steps:

setting at least one standard setting characterizing the measurement via a user interface of the CT device,
automatic configuring of the CT filter electronics on the basis of the settings performed, by a CT system computer,
radiographing the object to be examined with X-ray-radiation emerging from the X-ray tube,
measuring or evaluating the CT signals with the detector and the configured CT measuring electronics.

In this case, the automatic configuring of the CT filter electronics takes place in a first embodiment of the method according to the invention by selecting a filter from a number of filters present in the CT filter electronics.

In a second embodiment of the method according to the invention, the automatic configuring of the CT filter electronics takes place by the calculation of filter coefficients, the filtering behavior of the filter electronics being determined by these filter coefficients.

Among the standard settings characterizing the measurement, one or more of the following settings may advantageously be performed:

activation or deactivation of a spring focus mode,
activation or deactivation of a high-resolution comb,
designation of the body region concerned,
choice of the convolution kernel.

An embodiment of the invention also proposes a computer software product which, when it runs on a computing device connected to a computed tomography device, calculates on the basis of standard setting pre-selections characterizing the measurement a filtering function by which a correspondingly adapted configuration of the filter electronics takes place, so that a desired image quality is achieved.

BRIEF DESCRIPTION OF THE DRAWINGS

Further advantages, features and properties of the present invention are explained in more detail below on the basis of exemplary embodiments, with reference to the accompanying figures.

DETAILED DESCRIPTION OF THE PREFERRED EMBODIMENTS

Figure 1:
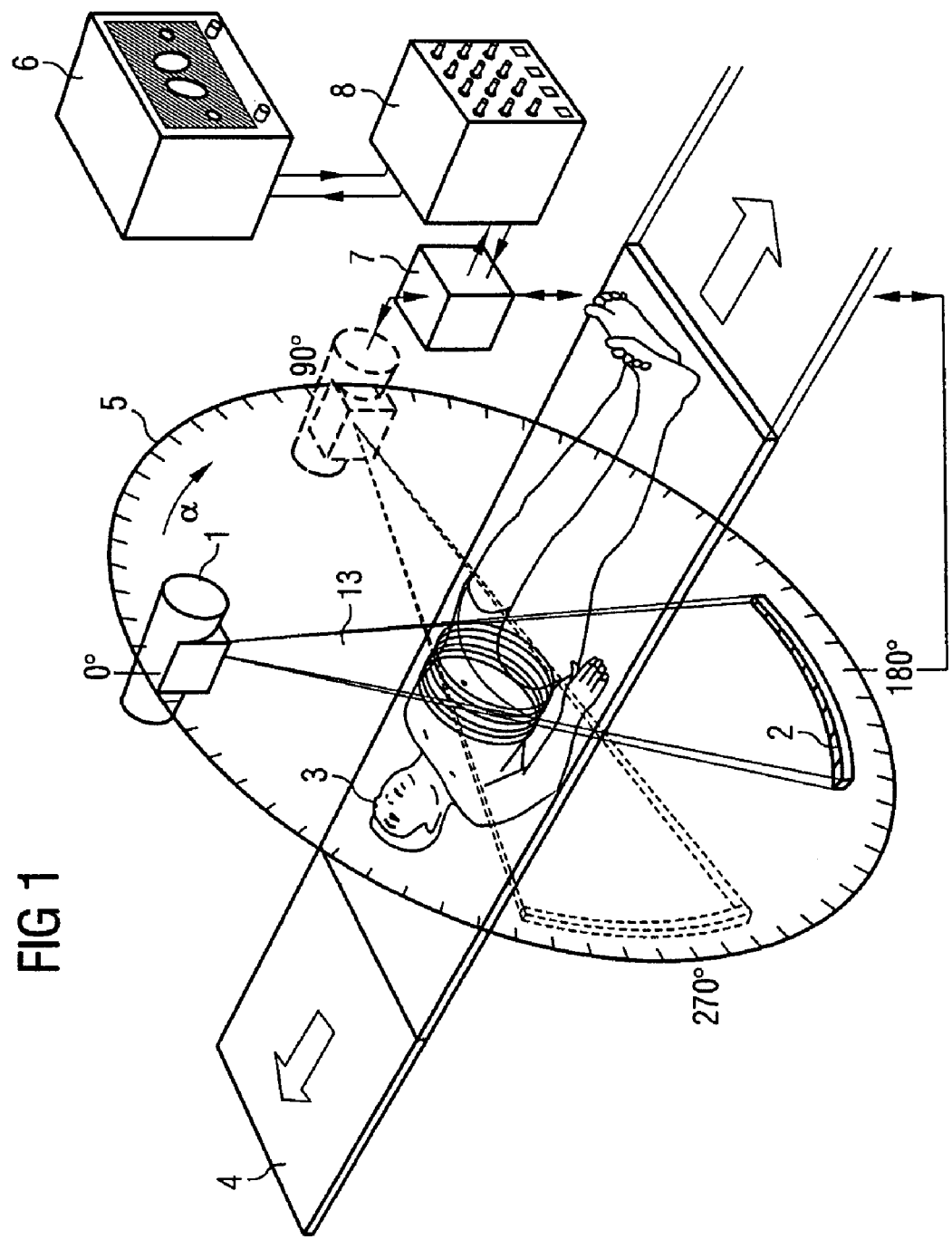
FIG. 1 schematically shows a computed tomography device according to an embodiment of the present invention, FIG. 2 schematically shows a flow diagram according to a first exemplary embodiment of the present invention, FIG. 3 schematically shows a flow diagram according to a second exemplary embodiment of the present invention.

In FIG. 2, the flow diagram according to a first exemplary embodiment of the present invention is represented. In step S1, the user, generally the doctor, performs a setting of a number of predetermined standard settings of the CT device via a user interface. This user interface is provided, for example, by a monitor 6 and/or a keyboard of the CT device represented in FIG. 1. It is possible, for example, in a step S1.1 to choose whether or not the CT measurement is to take place in spring focus mode. In a further step S1.2, the user is faced with the decision as to whether or not the measurement is to take place with a high-resolution comb. In the next-following step S1.3, the user inputs the body region to be measured. In a fourth step S1.4, the user has the possibility of setting the desired sharpness-contrast ratio by choosing the corresponding convolution kernel.

The substeps S1.1 to S1.4, presented in step S1, are only a few examples of possible standard settings of the CT device to carry out a measurement with a specific configuration of the CT device. What is meant by "configuration" according to the invention is both a mechanical and technical preparation of the CT device by the choice of predetermined scanning parameters (spring focus, high-resolution comb) and a non-mechanical preparation by the choice of predetermined evaluation parameters (body region, convolution kernel).

Activation of the spring focus according to S1.1 refers to the focus on the anode integrated in the X-ray tube being moved counter to the direction of movement of the tube and being consequently held fixed in place in the reference system of the space during the time of two successive measurements. After that, the focus springs back under electromagnetic control to its original position on the anode and the operation is repeated. Since the detector is continuously advanced, this procedure produces two measured projections, offset in each other, for each focusing position in the reference system of the space. This consequently doubles the scanning rate, whereby the local resolution can be increased.

On activation of the high-resolution comb according to S1.2, thin lamellae of a highly absorbent material, which as such represent to a certain extent the teeth of a comb, are positioned over the detector in such a way that they respectively cover the joint between two detector elements. Depending on their width, they reduce the detector apparatus, whereby a higher local resolution can be achieved. However, this also has the effect of reducing the dosing efficiency of the overall system, for which reason such a high-resolution comb is used only for high-contrast scans.

If the user makes a decision according to step S1.3 with respect to a body region to be measured (for example skull, soft tissue, etc.), the frequency content of the CT signal to be measured is fixed. In the case of skull scans, for example, more high-frequency components in the CT signal are taken into consideration, which does lead to a better spatial resolution of the image, though at the same time with higher image noise. Conversely, when scanning soft tissue zones, low-frequency components are primarily taken into consideration, which does reduce the resolution but at the same time lowers the image noise. This interaction between resolution and image noise can similarly be influenced according to step S1.4 by the choice of the convolution kernel.

An embodiment of the present invention consequently includes converting the configuration of the CT device established by choice of the scanning and evaluation parameters into parameters of the electronics, by which the overall measuring electronics are automatically configured in an optimum way. This ultimately indicates optimum adaptation of the frequency response of the measuring electronics to the configured CT system, and indeed for this to occur already during the measurement.

According to the first exemplary embodiment of the invention, as represented in FIG. 2 in the form of a sequence of steps, the measuring electronics 7, represented for example in FIG. 1, comprise a series of filters (filter 1 to filter N). The analog-digital part which the measuring electronics 7 also have is not represented. The filtering electronics serve for filtering and preparing the measurement signal output by the beam receiver 2 (detector) and digitized by the analog-digital part of the measuring electronics. In this case, each filter corresponds to a defined configuration of the CT device, as performed in step S1. Each filter is adapted to the configuration of the CT device assigned to it, in such a way that it produces an optimum or desired image quality.

The conversion consequently takes place according to step S2 by the CT system computer 8 represented in FIG. 1, which detects the configuration set in step S1 and assigns it to the corresponding filter. In step S3, the measurement is then carried out with the selected filter.

In FIG. 3, a modification of the method from FIG. 2 is represented. As in step S1 of the method represented in FIG. 2, the CT device is configured according to step S4. As a difference from FIG. 2, however, the measuring electronics 7 do not comprise a series of filters but complex adaptive electronics, which are configured by corresponding coefficients. As a result, they have a correspondingly desired optimum electronics filtering behavior adapted to the configuration of the CT device.

The coefficients mentioned are calculated according to step S5 by the CT system computer 8 and fed to the measuring electronics 7, for example in the form of a table. Such a table may have 512, 1024 or more values. On the basis of the calculated coefficients, the measuring electronics 7 carry out a CT measurement according to step S6 in such a way that, for example, spurious aliasing signals and noise elements in the actual useful band of the measured CT signal are optimally filtered out.

The essential component of adaptive measuring electronics, as intended for use in an embodiment of the present invention, resides in a configurable analog-digital converter (AD converter), in which filtering constitutes part of the converter concept. The type and manner of filtering can be explicitly fixed by input of defined filter coefficients. The selection or calculation of the coefficients is based on the desired frequency response which the AD converter is intended to have as part of its filtering property. In this case, the frequency response is dependent on the one hand on the integration time of the AD converter, by which the CT signal is band-limited according to the Nyquist theorem. On the other hand, the configuration of the CT device must be taken into consideration.

For example, given an integration time of $\tau=200$ µm, frequency components up to a maximum of $0.5*1/200$ µm$=2.5$ kHz are sampled. Frequency components above 2.5 kHz, on the other hand, are subject to aliasing and are filtered out from the signal.

This does not apply if the CT device is operated in spring focus. The spring focus of a CT device has the effect of additionally generating higher-frequency components in the CT signal, which lie in the range of several kHz. It has been found in simulations that the first harmonic caused by the spring focusing movement should be allowed to pass completely through, whereas higher-frequency components should be suppressed. The spring focusing frequency is half the sampling frequency $$f_{spring}=\tfrac{1}{2}f_{sample},$$

that is in the above example 2.5 kHz. The frequency of the first harmonic then lies at $f_{sample}=5$ kHz, that is to say it is equal to the sampling frequency. However, the optimum frequency response (the optimum filter function) of the AD converter is also based on the form of the space-time dependence of the spring focusing movement (for example trapezoidal, triangular, rectangular, etc.).

A further aspect determining the frequency response is the actual desired frequency content of the CT signals. If, for example, a high spatial resolution of the image data is to be achieved at the same time as tendentially higher image noise, high-frequency components must be taken along in the CT signal. This is advisable, for example, in the case of high-contour skull scans. If, on the other hand, higher-frequency components are cut off, the resolution is reduced but at the same time the image noise is lowered. This is of interest for example when scanning soft tissue zones, for which a low contrast is adequate.

There is consequently a correlation between resolution and image noise, the ratio of which can be fixed in particular by the convolution kernel (sharpness-contrast ratio) determining the CT image reconstruction, for example according to step S1.4. The advantages of the method according to an embodiment of the invention, represented in FIG. 2 and FIG. 3, can be summarized as follows:

The adaptation of the measuring electronics, in particular their filtering behavior, to the respective configuration of the CT device, allows the informational content of the CT measurement signal to be better utilized. This results in, on the one hand, lower image noise but on the other hand—as simulations showed—also an associated reduction in the dose of the order of 16%.

In addition, a further CT device configuration input mode—for example in the form of a further step S1.5 in the methods of the two FIGS. 1 and 2—allows the image quality of the device of a different manufacturer or of an older model to be imitated as accurately as desired. This is done in order to make it easier for customers who have been used to a certain noise and sharpness impression, often over years or decades, to handle the CT device according to an embodiment of the invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A computed tomography device, comprising:
    an X-ray tube for radiographing an object to be examined with X-radiation;
    a beam receiver for measuring the X-radiation transmitted through the object and for outputting measurement signals;
    a user interface, via which at least one standard setting of the device characterizing the measurement is adapted to be set in the form of at least one of different evaluation and scanning parameters;
    measuring electronics, including configurable filter electronics for filtering and preparing the measurement signals; and
    a system computer for configuring the filter electronics based upon the at least one standard setting set before the measurement via the user interface and for evaluating the measurement results.

2. The computed tomography device as claimed in claim 1, wherein the configuration of the filter electronics takes place by selection of a filter from a number of filters present in the filter electronics.

3. The computed tomography device as claimed in claim 2, wherein, in a first standard setting, whether or not the measurement takes place in spring focus mode is set.

4. The computed tomography device as claimed in claim 2, wherein, in a second standard setting, whether or not the measurement takes place with a high-resolution comb is set.

5. The computed tomography device as claimed in claim 2, wherein, in a third standard setting, the body region for which the measurement takes place is set.

6. The computed tomography device as claimed in claim 2, wherein, in a fourth standard setting, the convolution kernel is set.

7. The computed tomography device as claimed in claim 1, wherein the configuration of the filter electronics takes place by the calculation of filter coefficients, the filtering behavior of the filter electronics being determined by these filter coefficients.

8. The computed tomography device as claimed in claim 7, wherein, in a first standard setting, whether or not the measurement takes place in spring focus mode is set.

9. The computed tomography device as claimed in claim 7, wherein, in a second standard setting, whether or not the measurement takes place with a high-resolution comb is set.

10. The computed tomography device as claimed in claim 7, wherein, in a third standard setting, the body region for which the measurement takes place is set.

11. The computed tomography device as claimed in claim 7, wherein, in a fourth standard setting, the convolution kernel is set.

12. The computed tomography device as claimed in claim 1, wherein, in a first standard setting, whether or not the measurement takes place in spring focus mode is set.

13. The computed tomography device as claimed in claim 12, wherein, in a second standard setting, whether or not the measurement takes place with a high-resolution comb is set.

14. The computed tomography device as claimed in claim 13, wherein, in a third standard setting, the body region for which the measurement takes place is set.

15. The computed tomography device as claimed in claim 14, wherein, in a fourth standard setting, the convolution kernel is set.

16. The computed tomography device as claimed in claim 1, wherein, in a second standard setting, whether or not the measurement takes place with a high-resolution comb is set.

17. A method of computed tomography (CT) imaging, comprising the steps of:
    setting at least one standard setting characterizing a measurement via a user interface of a computed tomography device;
    automatically configuring CT filter electronics based on the at least one setting set, using a CT system computer;
    radiographing an object to be examined with X-ray-radiation emerging from an X-ray tube; and
    at least one of measuring and evaluating CT signals with a detector and the configured CT filter electronics.

18. The method as claimed in claim 17, wherein the automatic configuring of the CT filter electronics takes place by selecting a filter from a number of filters present in the CT filter electronics.

19. The method as claimed in claim 18, wherein, among the at least one standard setting characterizing the measurement, at least one of the following settings is performed:
    at least one of activation and deactivation of a spring focus mode;
    at least one of activation and deactivation of a high-resolution comb;
    designation of the body region concerned; and
    choice of the convolution kernel.

20. The method as claimed in claim 17, wherein the automatic configuring of the CT filter electronics takes place by the calculation of filter coefficients, the filtering behavior of the filter electronics being determined by these filter coefficients.

21. The method as claimed in claim 20, wherein, among the at least one standard setting characterizing the measurement, at least one of the following settings is performed:
    at least one of activation and deactivation of a spring focus mode;
    at least one of activation and deactivation of a high-resolution comb;
    designation of the body region concerned; and
    choice of the convolution kernel.

22. The method as claimed in claim 17, wherein, among the at least one standard setting characterizing the measurement, at least one of the following settings is performed:
    at least one of activation and deactivation of a spring focus mode;
    at least one of activation and deactivation of a high-resolution comb;
    designation of the body region concerned; and
    choice of the convolution kernel.

23. A non-transitory computer readable medium adapted to instruct a computing device to perform, when run on the computing device connected to a computed tomography device:
    calculating, based upon standard setting pre-selections characterizing a computed tomography measurement, a filtering function; and
    configuring filter electronics based on the calculated filtering function, so that a desired image quality is achieved.

24. A non-transitory computer readable medium, adapted to instruct a computing device to perform, when run on the computing device connected to a computed tomography device, the method of claim 17.

25. A non-transitory computer readable medium, adapted to instruct a computing device to perform, when run on a computing device connected to a computed tomography device, the method of claim 18.

26. A non-transitory computer readable medium, adapted to instruct a computing device to perform, when run on a computing device connected to a computed tomography device, the method of claim 20.

27. A non-transitory computer readable medium, adapted to instruct a computing device to perform, when run on a computing device connected to a computed tomography device, the method of claim 22.

28. A computed tomography device, comprising:
X-ray means for radiographing an object to be examined with X-radiation;
means for measuring the X-radiation transmitted through the object and for outputting measurement signals;
means for setting at least one standard setting of the device characterizing the measurement;
configurable filtering means for filtering and preparing the measurement signals; and
means for configuring the configurable filtering means based upon the at least one standard setting set before the measurement, and for evaluating the measurement results.

29. The computed tomography device as claimed in claim 28, wherein at least one standard setting of the device characterizing the measurement is adapted to be set in the form of at least one of different evaluation and scanning parameters.

30. The computed tomography device as claimed in claim 28, wherein the configuration of the configurable filtering means takes place by selection of a filter from a number of filters present in the configurable filtering means.

31. The computed tomography device as claimed in claim 28, wherein the configuration of the configurable filtering means takes place by the calculation of filter coefficients, the filtering behavior of the configurable filtering means being determined by these filter coefficients.

* * * * *